US00PP31308P3

(12) United States Plant Patent
Hansen

(10) Patent No.: US PP31,308 P3
(45) Date of Patent: Dec. 31, 2019

(54) ***PHLOX* PLANT NAMED 'KUNG FUCHSIA'**

(50) Latin Name: ***Phlox* hybrid**
Varietal Denomination: Kung Fuchsia

(71) Applicant: Hans A Hansen, Zeeland, MI (US)

(72) Inventor: Hans A Hansen, Zeeland, MI (US)

(73) Assignee: Walters Gardens Inc., Zeeland, MI (US)

( * ) Notice: Subject to any disclaimer, the term of this patent is extended or adjusted under 35 U.S.C. 154(b) by 0 days.

(21) Appl. No.: 16/501,030

(22) Filed: Feb. 11, 2019

(65) Prior Publication Data

US 2019/0254214 P1 Aug. 15, 2019

Related U.S. Application Data

(60) Provisional application No. 62/710,258, filed on Feb. 14, 2018.

(51) Int. Cl.
*A01H 6/70* (2018.01)
*A01H 5/02* (2018.01)

(52) U.S. Cl.
USPC ..... Plt./320
CPC ..... *A01H 6/70* (2018.05)

(58) Field of Classification Search
USPC ..... Plt./320
CPC ..... A01H 5/02; A01H 6/70
See application file for complete search history.

*Primary Examiner* — Annette H Para

(57) ABSTRACT

A new and unique cultivar of garden *phlox* named *Phlox* 'Kung Fuchsia' multi-stemmed, short, upright, slowly-spreading habit with clean green, glossy, lanceolate leaves with exceptional powdery mildew resistance. Foliage is thick with stiff stocky stems. Sweetly fragrant flowers of bright fuchsia faces with light pink eye zones markings are produced on multiple branched peduncles and cover the top of the plant beginning early summer about two weeks prior typical *Phlox paniculata* cultivars. 'Kung Fuchsia' is especially suitable as a potted plant, for the garden, for attracting hummingbirds and butterflies, and for cut flower arrangements.

1 Drawing Sheet

Botanical classification: *Phlox* hybrid.
Variety denomination: 'Kung Fuchsia'.

BACKGROUND OF THE INVENTION

The present invention relates to a new and distinct cultivar of *Phlox* plant, known as *Phlox* 'Kung Fuchsia' and will be referred to hereafter by its cultivar name or the "new plant". The new plant was the result of a cross of *Phlox carolina* 'Lil' Cahaba' (not patented) as the female or seed parent and the male or pollen parent is unknown performed at a wholesale perennial nursery in Zeeland, Mich. in the summer of 2013. The new plant was initially given the breeder code 13-481-1 throughout subsequent evaluations at the same nursery. 'Kung Fuchsia' has been asexually propagated by stem cuttings in the greenhouses at the same nursery in Zeeland, Mich. since 2015. The unique characteristics of the new plant have been found to be reproducible and stable in successive generations of asexually propagated plants and the resultant plants have been found to be identical to the original selection.

No plants of *Phlox* 'Kung Fuchsia' have been sold or disclosed, in this country or anywhere in the world, prior to the priority date of this application, nor has any disclosure of the new plant been made before the priority date of this application except that which was disclosed within one year of the priority date of this application, and was either derived directly or indirectly from the inventor.

BRIEF SUMMARY OF THE PLANT

*Phlox* 'Kung Fuchsia' is unique from its parents and all other tall garden *phlox* or other *Phlox* known to the inventor.

The new plant differs from the female parent 'LiL' Cahaba' in that the female parent has different colored flowers. The new plant is more compact with stiffer stems and thicker and darker green leaves. Compared to the male parent is not possible. The most closely comparison cultivar known to the inventor is *Phlox* 'Cloudburst' U.S. Plant patent application Ser. No. 15/732,194. Compared with 'Cloudburst' the new plant has more upright stems, flowering more in the distal one-half of the plant, and the flower color is more fuchsia and less purple. 'Kung Fuchsia' differs from all other *phlox* known to the inventor in the following repeatedly observed traits in combination:

1. Plants of short upright habit, slowly spreading by short rhizomes, producing clean, glossy, clean green, lanceolate leaves;
2. Showing exceptional powdery mildew resistance;
3. Multiple branched, stems produce rounded mounds of flowers starting very early in the season;
4. Sweetly fragrant flowers on strong stiff stems of about 42.0 cm tall producing sweetly-fragrant, bright fuchsia flower faces with light pink eye zones markings;
5. Flowers cover the entire top of the plant;
6. Flowering beginning in early-summer about two weeks prior to typical *Phlox paniculata* cultivars and re-blooming through late-summer.

BRIEF DESCRIPTION OF THE DRAWINGS

The photographs of the new plant demonstrate the unique traits of 'Kung Fuchsia' and the overall appearance of the plant at two-years-old grown in a full sun trial garden in Zeeland, Mich. The colors are as accurate as reasonably possible with color reproductions. Variation in ambient light spectrum, source and direction may cause the appearance of minor variation in color.

DETAILED BOTANICAL DESCRIPTION

Figure 1:
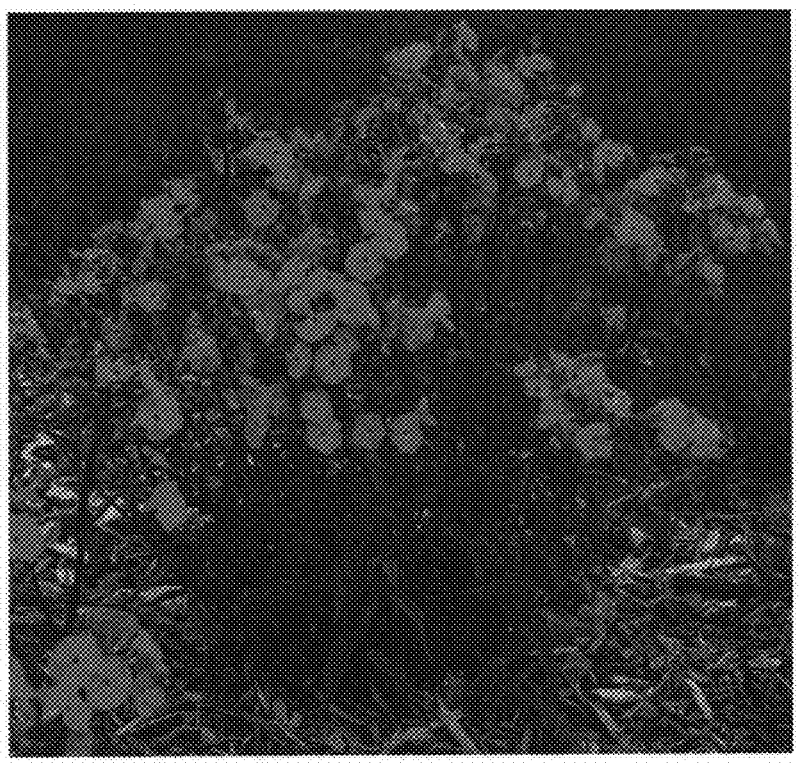
FIG. 1 shows the new plant in peak flower in the landscape.
Figure 2:
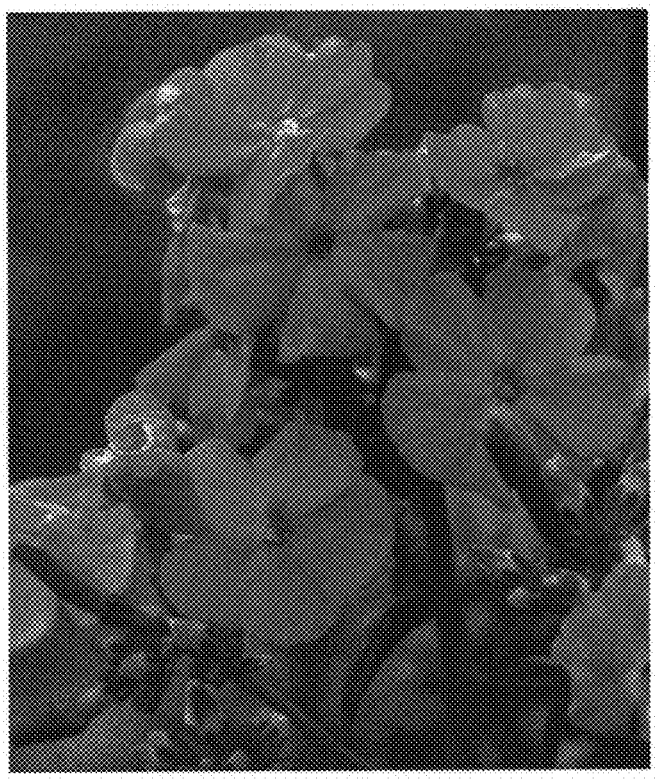
FIG. 2 shows a close-up of the floriferous flower head with flowers and buds.

The following descriptions and color references are based on the 2015 edition of The Royal Horticultural Society Colour Chart except where common dictionary terms are used. *Phlox* 'Kung Fuchsia' has not been observed under all possible environments. The phenotype may vary slightly with different growing environments such as temperature, light, fertility, soil pH, moisture and maturity levels, but without any change in the genotype. The following observations and size descriptions are based on two-year-old plants in the full sun trial garden of a wholesale perennial nursery in Zeeland, Mich. with supplemental fertilizer and water as needed.

Botanical classification: *Phlox* hybrid;

Parentage: Female or seed parent *Phlox carolina* 'Lil' Cahaba'; male or pollen parent unknown;

Plant habit: Hardy herbaceous perennial, densely upright, producing about 22 rigid upright stems; flowering and about 45.0 cm tall and about 50.0 cm wide; flowering begins early summer in Michigan and continuing for about 5 weeks;

Propagation: Stem cuttings; rooting in about 14 days;

Time to produce finished crop in 3.8 liter pots: About 8 to 10 weeks; moderate rate of growth;

Root: Primary roots to about 1.0 mm thick; secondary fibrous and freely branching; color creamy white to tan depending on soil type;

Leaves: Simple, opposite, lanceolate; entire margin; narrowly acute apex; rounded to attenuate base;

Leaf size: To about 70.0 mm long by about 14.0 mm wide, average about 65.0 mm long by about 12.0 mm wide;

Leaf surfaces: Glabrous and lustrous abaxial and adaxial;

Leaf color expanding: Abaxial nearest RHS 144B, adaxial nearest RHS 144A;

Leaf color at flowering: Abaxial nearest RHS 137B, adaxial nearest RHS 137A;

Foliage fragrance: None detected;

Veins: Pinnate; glabrous abaxial and adaxial; midrib about 1.0 mm wide at base, slightly sunken adaxial and raised abaxial;

Vein color: Abaxial midrib nearest RHS 145C, adaxial midrib nearest RHS 145C; other adaxial and abaxial veins same color as surrounding leaf;

Petiole: Leaves sessile;

Stems: Terete; stiff; wiry; strong; upright; glabrous; average about 40.0 cm long and 6.0 mm diameter at base;

Stem color: Nearest RHS 137A; becoming tinted with nearest RHS N186C distally;

Nodes: About nine per stem below flowers; average internode length about 4.4 cm;

Node color: Nearest RHS 137A;

Inflorescence: A loosely-branched compound corymb of about 100 flowers; about 17.0 cm long and 11.0 cm across;

Flowers: Perfect; salverform with flat face and long fused tube; actinomorphic; typically with five petals; about 25.0 mm long total with tube about 20.0 mm long; face about 20.0 mm across; attitude upright to outward;

Flower longevity: About 5 days on plant or as cut flower; self-cleaning;

Flower fragrance: Faint to lightly sweet;

Buds one to two days prior to opening: Narrowly oblanceolate, to nearly clavate; acute apex with petals twisted about each other; base fused; about 30.0 mm long and 3.0 mm diameter in tube and swollen to 5.0 mm diameter toward apex of convolute petals;

Bud color: Petals and base nearest RHS 60D;

Petals; Five; margin entire; apex rounded; base fused into tube; abaxial and adaxial limb glabrous, abaxial tube surface puberulent, adaxial tube glabrous except pubescent in region about 5.0 mm to 10.0 mm from base;

Petal size: Basal 20.0 mm fused into tube, to a diameter of about 3.0 mm; limbs about 11.0 mm across, and face about 9.0 mm long; imbricate about 3.0 mm of the petals to either side;

Petal color: Adaxial face nearest RHS N57A with light patches toward center nearest RHS 75C toward base; abaxial limb nearest RHS 71D toward center and nearest RHS 73A toward apex; adaxial tube nearest RHS 145C toward base with pubescence white nearest RHS NN155D and distal 13.0 mm of tube nearest RHS 57D, abaxial tube basal 3.0 mm nearest RHS 145C with distal 17.0 mm blend between RHS 67B and RHS 71D;

Androecium:

*Filaments.*—Typically five; adnate to adaxial petals except free in terminal 1.0 mm; varying lengths between 16.0 mm and 12.0 mm, less than 0.5 mm in diameter; white, nearest RHS NN155D.

*Anther.*—Five; oblong elliptic; basifixed; longitudinal; about 4.0 mm long by 1.0 mm wide; color nearest RHS 10A.

*Pollen.*—Abundant; color nearest RHS 17A.

Gynoecium: One pistil per flower; to about 20.0 mm long;

*Style.*—Terete; about 16.0 mm long and less than 0.5 mm diameter; color base nearest RHS 145D, distal section nearest RHS 64B.

*Stigma.*—Trifurcate in the distal 1.5 mm, less than 0.25 mm in diameter; persistent after flower abscission; color nearest RHS 150C.

*Ovary.*—Superior; globose; about 2.5 mm long and 1.5 mm diameter; color nearest RHS 144A.

Calyx: Tubular; to about 4.0 mm long and 3.0 mm wide at apex;

Sepals: Five; lanceolate; narrowly acute apex, margin entire; base fused; surface matte and sparsely puberulent abaxial and lustrous adaxial; individually about 4.0 mm long and 1.5 mm wide; fused in basal 3.0 mm;

Sepal color: Abaxial apex nearest RHS 145A; adaxial nearest RHS 145B;

Peduncle: Glabrous, stiff, strong, upright, terete; about 40.0 cm long and 3.5 mm diameter at base of flower branches; branches to about 15.0 cm long and 2.0 mm diameter at base;

Peduncle color: Nearest RHS 146A;

Pedicel: Terete; glabrous; to about 2.0 mm long and 1.0 mm diameter;

Pedicel color: Nearest RHS 145B; Fruit and seeds have not yet been observed.

Hardiness and culture: The new plant grows best with plenty of moisture and adequate drainage; hardy to at least from USDA zone 5 through 8.

Disease and pest resistance: *Phlox* 'Kung Fuchsia' demonstrated the excellent powdery mildew resistance caused by *Erysiphe cichoracearum* under conditions of intense pressure that would normally show symptoms.

I claim:

1. A new and distinct cultivar of hybrid *Phlox* plant named 'Kung Fuchsia', as herein described and illustrated.

* * * * *